United States Patent
Choi (10) Patent No.: US 11,666,707 B2
(45) Date of Patent: Jun. 6, 2023

(54) DISPOSABLE SYRINGE SET HAVING IMPROVED COMPATIBILITY

(71) Applicant: SEWOON MEDICAL CO., LTD., Cheonan-si (KR)

(72) Inventor: Dae Han Choi, Gwangju (KR)

(73) Assignee: SEWOON MEDICAL CO., LTD., Cheonan-si (KR)

( * ) Notice: Subject to any disclaimer, the term of this patent is extended or adjusted under 35 U.S.C. 154(b) by 166 days.

(21) Appl. No.: 16/929,351

(22) Filed: Jul. 15, 2020

(65) Prior Publication Data

US 2020/0345939 A1 Nov. 5, 2020

Related U.S. Application Data

(63) Continuation of application No. PCT/KR2018/004994, filed on Apr. 30, 2018.

(30) Foreign Application Priority Data

Jan. 31, 2018 (KR) .................. 20-2018-0000485

(51) Int. Cl.
- *A61M 5/31* (2006.01)
- *A61M 5/32* (2006.01)
- *A61M 5/34* (2006.01)

(52) U.S. Cl.
CPC ........ *A61M 5/3134* (2013.01); *A61M 5/3293* (2013.01); *A61M 5/346* (2013.01);
(Continued)

(58) Field of Classification Search
CPC ...... A61M 5/3293; A61M 5/34; A61M 5/347; A61M 60/865
See application file for complete search history.

(56) References Cited

U.S. PATENT DOCUMENTS

| | | | |
|---|---|---|---|
| 1,180,051 A * | 4/1916 | Laurent ................ | A61M 5/343 604/243 |
| 1,274,081 A * | 7/1918 | Riethmueller ......... | A61M 5/46 604/117 |

(Continued)

FOREIGN PATENT DOCUMENTS

| JP | 2016538954 A | 12/2016 |
|---|---|---|
| JP | 2016539765 A * | 12/2016 |

(Continued)

OTHER PUBLICATIONS

International Search Report of PCT/KR2018/004994 dated Oct. 26, 2018.

*Primary Examiner* — William R Carpenter
(74) *Attorney, Agent, or Firm* — Nicholas Park (57) ABSTRACT

A disposable syringe set includes a syringe barrel in which a medicinal fluid inlet is formed and a plunger is fitted and coupled to an opening at the other side; a first screw-coupling portion formed on an outer circumference of the medicinal fluid inlet; a syringe needle hub in which a syringe needle is coupled to one end and an inner side at the other end is fitted and coupled to the outer circumference of the medicinal fluid inlet; and a second screw-coupling portion formed on an inner circumference of the syringe needle hub and configured to be coupled to the first screw-coupling portion. The first screw-coupling portion is formed as a female-thread-type coupling portion whose diameter is smaller than a reference diameter of the medicinal fluid inlet. The second screw-coupling portion is formed as a male-thread-type coupling portion configured to be coupled to the female-thread-type coupling portion.

1 Claim, 5 Drawing Sheets

(52) U.S. Cl.
CPC ..... *A61M 5/347* (2013.01); *A61M 2005/3107* (2013.01); *A61M 2205/273* (2013.01)

(56) References Cited

U.S. PATENT DOCUMENTS

| | | | | |
|---|---|---|---|---|
| 2,423,762 | A * | 7/1947 | Everett | F16B 33/02 285/333 |
| 3,468,309 | A * | 9/1969 | Drewe | A61M 5/347 604/206 |
| 8,052,641 | B2 | 11/2011 | Heijima et al. | |
| 2002/0010433 | A1 * | 1/2002 | Johnson | A61M 5/347 604/241 |
| 2002/0173753 | A1 * | 11/2002 | Caizza | A61M 5/3234 604/241 |
| 2003/0050602 | A1 * | 3/2003 | Pettis | A61M 37/0015 604/117 |
| 2006/0200085 | A1 * | 9/2006 | Watts | A61L 2/07 604/240 |
| 2008/0033347 | A1 * | 2/2008 | D'Arrigo | A61M 5/347 604/93.01 |
| 2011/0202035 | A1 * | 8/2011 | Voellmicke | A61M 5/008 604/218 |
| 2013/0317451 | A1 * | 11/2013 | Del Vecchio | A61M 5/345 604/241 |
| 2015/0112252 | A1 * | 4/2015 | Eggert | A61M 5/34 604/87 |
| 2016/0067422 | A1 * | 3/2016 | Davis | A61M 5/3134 604/192 |
| 2017/0043102 | A1 * | 2/2017 | Moses | A61M 5/484 |

FOREIGN PATENT DOCUMENTS

| | | |
|---|---|---|
| KR | 101008476 B1 | 1/2011 |
| KR | 1020150018336 A | 2/2015 |
| KR | 101679166 B1 | 11/2016 |

* cited by examiner

DISPOSABLE SYRINGE SET HAVING IMPROVED COMPATIBILITY

CROSS-REFERENCE TO RELATED APPLICATION

This application is a continuation of International Application No. PCT/KR2018/004994 filed on Apr. 30, 2018, which claims priority to and the benefit of Korean Patent Application No. 20-2018-0000485, filed on Jan. 31, 2018, the disclosure of which is incorporated herein by reference in its entirety.

BACKGROUND

Field of the Invention

The present invention relates to a disposable syringe set with improved engageability, and more particularly, to a disposable syringe set with improved engageability in which a screw-coupling part is formed at each of an outer circumference of a medicinal fluid inlet, which is configured to protrude from a distal end portion of a syringe barrel, and an inner circumference of a syringe needle hub, which is coupled to the outer circumference of the medicinal fluid inlet, so that the medicinal fluid inlet and the syringe needle hub may be firmly coupled and easily detached and, when the medicinal fluid inlet and the syringe needle hub are coupled to another syringe needle hub or syringe barrel, firm coupling is possible and leakage of drug does not occur.

Discussion of Related Art

A generally-used syringe or syringe set includes a cylindrical syringe barrel in which a medicinal fluid is stored, a piston-type plunger inserted into an opening at one side of the syringe barrel and configured to draw drug into the syringe barrel or forcibly discharge the medicinal fluid filled in the syringe barrel to the outside of the syringe barrel, and a medicinal fluid inlet of a predetermined length which is formed to protrude a predetermined length from a central portion at the front of the syringe barrel so that a syringe needle hub, to which a syringe needle is coupled, is able to be fitted and fixed thereto and which is configured to supply the medicinal fluid of the syringe barrel to the syringe needle through a communication path formed at a central portion thereof.

Generally, such a syringe is used to inject a medicinal fluid by connecting the syringe needle to the medicinal fluid inlet and inserting the needle directly into the patient's skin but, when necessary, is also used when additionally supplying a medicinal fluid by separating the syringe needle and connecting another medicinal fluid supply device or medicinal fluid supply means to the medicinal fluid inlet.

Figure 1:
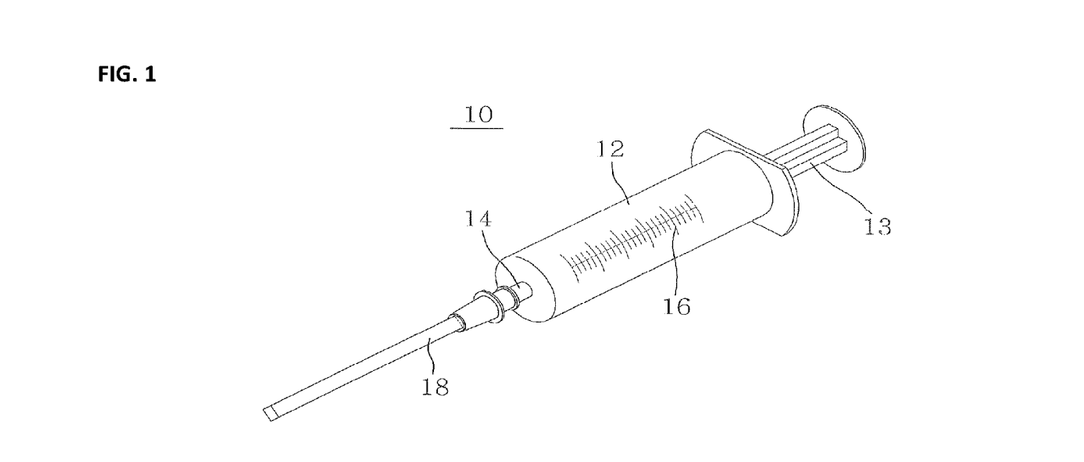
FIG. 1 is a coupled perspective view of a conventional syringe set according to an embodiment.
Figure 2:
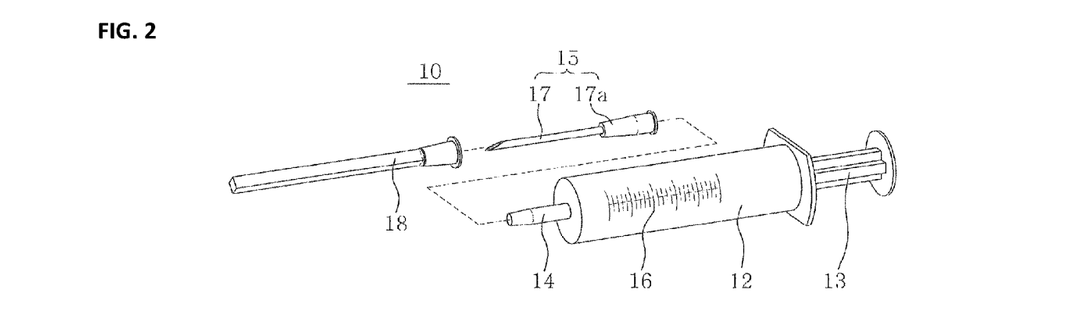
FIG. 2 is a partially exploded perspective view of a conventional syringe set according to an embodiment.

The conventional, most common syringe set is illustrated in FIGS. 1 and 2.

The configuration of the syringe will be described in more detail with reference to FIGS. 1 and 2. A syringe 10 includes a cylindrical syringe barrel 12 in which a medicinal fluid to be injected is stored and a plunger 13 fitted and coupled to the syringe barrel 12 so as to be inserted into the syringe barrel 12 through an opening at one side of the syringe barrel 12 and, while moving back and forth, draw the medicinal fluid into the syringe barrel 12 or extrude the drawn-in medicinal fluid out of the syringe barrel, wherein scales 16 are marked on an outer circumference of the syringe barrel 12 so as to recognize the capacity of the medicinal fluid filled inside the syringe barrel 12.

Also, a small-diameter medicinal fluid inlet 14 is formed at the other side of the syringe barrel 12 so as to protrude a predetermined length toward the outside of the syringe barrel 12 so that a syringe needle 15 may be coupled to the medicinal fluid inlet 14.

Also, the syringe needle 15 coupled to the medicinal fluid inlet 14 of the syringe barrel 12 is formed of a structure including a syringe tip 17 made of metal or plastic that has a sharp end so as to be inserted into the body of an injection object at a predetermined depth and a hub 17a formed at one side end portion of the syringe tip 17 to couple the syringe tip 17 to the medicinal fluid inlet 14 of the syringe barrel 12.

Also, an outer side of the syringe needle 15 is covered with a protective cap 18 for protection and management for handling and safety of the syringe tip 17 provided at a distal end portion of the syringe needle 15.

In order to allow an injection to be performed, the current syringe 10 having the above-described configuration and structure is provided in a form in which the syringe needle 15, to which the protective cap 18 is coupled, is coupled to the medicinal fluid inlet 14 of the syringe barrel 12, provided in a state in which the syringe barrel 12 and the syringe needle 15 are separated, or has a form in which the syringe barrel 12 and the syringe needle 15 are packaged and provided separately. Thus, in order to perform an injection, the hub 17a, to which the syringe needle 15 is coupled, is fitted and fixed to the medicinal fluid inlet 14 of the syringe barrel 12, the protective cap 18 is separated from the syringe needle 15, the syringe needle is inserted into the body of a patient, and then the plunger 13 provided in the syringe barrel is operated so that the drug filled inside the syringe barrel is injected into the body of the patient.

In the use of the syringe having the above-described configuration and structure, due to the structure in which, when coupling the syringe needle 15 to the medicinal fluid inlet 14 of the syringe barrel 12, the hub 17a of the syringe needle 15 is forcibly fitted to the outer circumference of the medicinal fluid inlet 14 of the syringe barrel 12, when nurses separate the protective cap from the syringe needle during the process of preparing a drug to be injected or in order to perform an injection on a patient, the syringe needle is also separated from the medicinal fluid inlet of the syringe barrel. Thus, an inconvenience of having to repeat the action of coupling the hub again to the medicinal fluid inlet has occurred frequently. Even when separating the syringe needle from the syringe barrel after performing an injection, since the forcibly-fitted syringe needle is not easily separated from the medicinal fluid inlet, there has been an inconvenience of having to turn the syringe needle left and right with a great force in order to remove the syringe needle.

In order to reduce such inconveniences, a method in which, while the distal end portion of the hub of the syringe needle, which is coupled to the syringe barrel, is firmly pressed with the thumb of the hand holding the syringe barrel, the protective cap coupled to the syringe needle is separated therefrom using the thumb and the index finger of the other hand is used in some cases. However, even in such cases, the distal end portion of the protective cap and the distal end portion of the hub should be held with fingers of both hands, or some of the fingers have to be placed between the distal end portion of the protective cap and the distal end portion of the hub in order to separate the protective cap from the syringe needle. Thus, since an excessive force should be applied with fingers when separating the protective cap, there has always been an inconvenience for nurses when separating the protective cap.

Also, even in the case in which drug is supplied by connecting the syringe 10, which uses the forcibly fitting method, to a 3-way stopcock or the like or another medical device, when a force is applied to the plunger to inject a medicinal fluid by only holding the syringe barrel while the medicinal fluid inlet of the syringe is forcibly fitted and coupled, there is a risk that the medicinal fluid inlet of the syringe may be separated from the other medical device while the drug is being supplied. Thus, for nurses, there has always been a difficulty of having to inject a medicinal fluid while tightly holding a connecting portion of a medicinal fluid supply device, which is connected to a syringe, with the hand not holding the syringe.

Several new types of syringes have been proposed to solve the inconveniences caused by the method of forcibly fitting and coupling when connecting the medicinal fluid inlet, which is formed at the distal end portion of the syringe barrel of the syringe, and the syringe needle hub configured to be connected thereto and connecting the medicinal fluid inlet and another medical device.

For example, new types of syringes have been proposed in Korean Patent Registration No. 10-1228585 (Date of Registration: Jan. 25, 2013, Title of Invention: Disposable syringe), Korean Patent Registration No. 10-1479258 (Date of Registration: Dec. 29, 2014, Title of Invention: Disposable syringe), Korean Utility Model Registration No. 20-0475457 (Date of Registration: Nov. 26, 2014, Title of Invention: Disposable syringe), Korean Patent Registration No. 10-1435898 (Date of Registration: Aug. 25, 2014, Title of Invention: Filter needle integrated type syringe), Korean Patent Registration No. 10-1679166 (Date of Registration: Nov. 17, 2016, Title of Invention: Medical device for administration of liquid medicine), Korean Utility Model Registration No. 20-0474667 (Date of Registration: Sep. 26, 2014, Title of Invention: connector of medical kit), Korean Patent Registration No. 10-1177279 (Date of Registration: Aug. 21, 2012, Title of Invention: Stop-cock of 3-way type for medical treatment and medical kit connected to this stop-cock), and the like.

Figure 3:
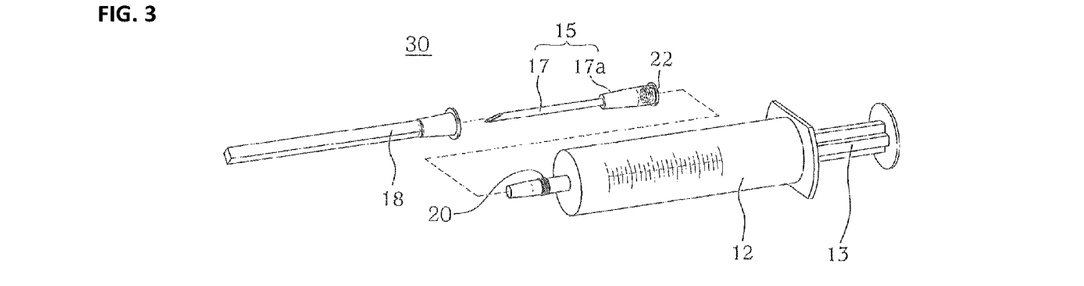
FIG. 3 is a partially exploded perspective view of a conventional, improved syringe set.

In the conventional "disposable syringe" and many other inventions, as illustrated in FIG. 3, a new coupling structure has been adopted in which, by forming a spiral outer engaging portion 20 having a predetermined pitch on the outer circumference of the medicinal fluid inlet 14 and forming a spiral inner engaging portion 22 on the inner circumference of the hub 17a of the syringe needle that is configured to be coupled to the medicinal fluid inlet 14, the syringe needle and the syringe barrel are engaged using a screw-coupling method.

The new type of syringe using the screw-coupling method provides an advantage in that, since coupling and separating the syringe needle and the syringe barrel is more convenient as compared to the conventional syringe using the forcibly fitting method, it is possible to significantly improve convenience of use in clinics and hospitals.

Also, even in the case in which drug is injected by connecting another medicinal fluid supply device to the medicinal fluid inlet of the syringe, since the other medicinal fluid supply device is coupled to the medicinal fluid inlet using a screw-coupling method, an inconvenience in which the drug leaks or the blood flow of the patient is reversed due to the other medicinal fluid supply device being arbitrarily separated from the medicinal fluid inlet does not occur. Therefore, the new type of syringe has been recognized as a very innovative product in the medical community.

However, when the new syringe and syringe needle hub, to which a screw-coupling method is applied, are applied to conventional other medical devices manufactured using the forcibly fitting coupling method that have been using the same method and having the same engagement structure since the middle of the 19$^{th}$ century when syringes were developed, there is an inconvenience in that the other medical devices may not be able to be coupled to the syringe and syringe needle hub.

That is, although, among the components of the syringe, the syringe barrel and the syringe needle may be provided with various standards in which sizes differ according to the capacity of the drug to be administered, the site in which the syringe will be used, and the like, syringes are produced and provided according to the same international standards in terms of an outer diameter of a medicinal fluid inlet provided at a distal end portion of the syringe barrel and an inner diameter of a syringe needle hub coupled to the syringe needle even when the capacities or sizes of syringe barrels differ or the sizes and uses of syringe needles differ. Thus, when only one of the outer diameter of the medicinal fluid inlet or the inner diameter of the syringe needle hub is formed according to a different standard, there is an inconvenience in that coupling with a syringe or a syringe needle using a different engagement method may not be possible.

The reason the screw-coupling method and the forcibly fitting method are not compatible is as follows. All screw portions formed on the conventional disposable syringes and medicinal fluid inlets thereof using the screw-coupling method are male screw portions, and thus smooth coupling and separation is possible to and from an engaging portion having a female screw portion configured to be coupled to the male screw portions, and tight sealing is possible after the coupling occurs. However, when the conventional disposable syringes and medicinal fluid inlets thereof using the screw-coupling method are coupled to a connector without a screw portion that uses the conventional forcibly fitting method, the diameter may be increased or decreased as much as the height of screw threads, and coupling with a non-screw type medicinal fluid connector may not be possible, or even when the coupling is performed, tight sealing may not be possible and leakage of drug may occur in some cases.

Figure 4:
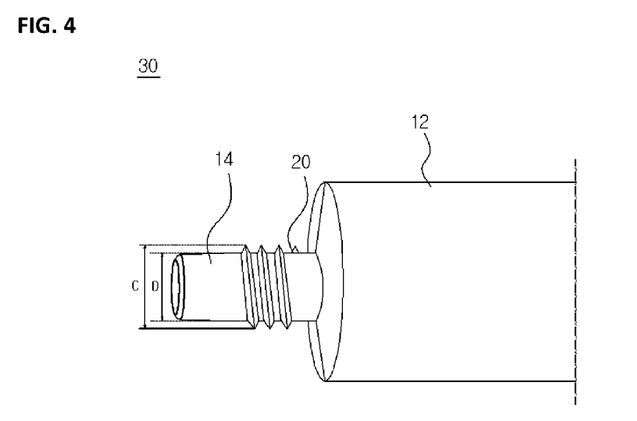
FIG. 4 is an enlarged view of a portion of a screw-coupling portion formed on an outer circumference of a medicinal fluid inlet in the conventional, improved syringe set illustrated in FIG. 3.

An enlarged view of the conventional medicinal fluid inlet using the screw-coupling method is illustrated in FIG. 4. That is, as illustrated in FIG. 4, screw threads of the engaging portion 20 are formed with a diameter C larger than a reference diameter D and thus protrude as much as the height of the threads from a reference circumferential surface formed with the reference diameter D. Therefore, the outer diameter of the medicinal fluid inlet is inevitably larger as much as the height of the screw threads than those of syringes and other medical devices using the forcibly fitting coupling method that are produced and distributed according to the same international standards, and thus coupling another non-screw type medicinal fluid connector to the engaging portion 20 having the screw threads formed thereon is not possible.

Accordingly, the present invention has been devised to provide an improved engagement structure that addresses the above-described problems of the conventional syringe having a screw-coupling structure, allows smooth coupling between parts using a screw-coupling method and parts not using the screw-coupling method, and prevents leakage of drug after coupling is performed.

RELATED ART DOCUMENTS

Patent Documents (Patent Document 1)
Korean Patent Registration No. 10-1177279 (Date of Registration: Aug. 21, 2012, Title of Invention: Stop-cock of 3-way type for medical treatment and medical kit connected to this stop-cock
(Patent Document 2)
Korean Patent Registration No. 10-1228585 (Date of Registration: Jan. 25, 2013, Title of Invention: Disposable syringe)
(Patent Document 3)
Korean Patent Registration No. 10-1435898 (Date of Registration: Aug. 25, 2014, Title of Invention: Filter needle integrated type syringe)
(Patent Document 4)
Korean Utility Model Registration No. 20-0474667 (Date of Registration: Sep. 26, 2014, Title of Invention: connector of medical kit)
(Patent Document 5)
Korean Utility Model Registration No. 20-0475457 (Date of Registration: Nov. 26, 2014, Title of Invention: Disposable syringe)
(Patent Document 6)
Korean Patent Registration No. 10-1479258 (Date of Registration: Dec. 29, 2014, Title of Invention: Disposable syringe)
(Patent Document 7)
Korean Patent Registration No. 10-1679166 (Date of Registration: Nov. 17, 2016, Title of Invention: Medical device for administration of liquid medicine)

SUMMARY OF THE INVENTION

The present invention has been devised to address the above-described problems of the conventional disposable syringes, particularly, disposable syringes having a screw-coupling structure, and is directed to providing a disposable syringe set with improved engageability with widely-used conventional non-screw type medical devices by, at the time of engagement between a disposable syringe having a screw-engaging structure and a non-screw type medical device that is configured to be connected to the disposable syringe, preventing leakage of drug and allowing the disposable syringe and the medical device to be compatibly used with other medical devices and syringes.

To achieve the above-described objective, a disposable syringe set with improved engageability according to the present invention has a structure including: a syringe barrel in which a medicinal fluid inlet of a predetermined length is formed to protrude from one side and a plunger is fitted and coupled to an opening at the other side; a first screw-coupling portion formed on an outer circumference of the medicinal fluid inlet; a syringe needle hub in which a syringe needle is provided and which is configured to be coupled to the outer circumference of the medicinal fluid inlet; and a second screw-coupling portion formed on an inner circumference of the syringe needle hub and configured to be coupled to the first screw-coupling portion, wherein the first screw-coupling portion is formed as a female-thread-type coupling portion having a diameter smaller than a reference diameter of the medicinal fluid inlet, the second screw-coupling portion provided on the inner circumference of the syringe needle hub is formed as a male-thread-type coupling portion configured to be coupled to the female-thread-type coupling portion, and a catching step having an annular shape is formed to protrude a predetermined height from an inner side end of the male-thread-type coupling portion formed on the inner circumference of the syringe needle hub.

Particularly, a valley of the female-thread-type coupling portion constituting the first screw-coupling portion and a thread of the male-thread-type coupling portion constituting the second screw-coupling portion form any one of a square thread form and a trapezoidal thread form in which surfaces of the valley and the thread are horizontal in a cross-sectional view, and the female-thread-type coupling portion and the male-thread-type coupling portion are coupled through coming in surface contact with each other.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION

A disposable syringe set with improved engageability (hereinafter abbreviated as "syringe set") according to the present invention includes a screw-type first screw-coupling portion formed on an outer circumference of a medicinal fluid inlet of a syringe barrel and a second screw-coupling portion formed on an inner circumference of a syringe needle hub, which is coupled to the medicinal fluid inlet of the syringe barrel, so as to correspond to the first screw-coupling portion, wherein the first screw-coupling portion is formed as a female-thread-type screw-coupling portion that is processed to have a diameter smaller than a reference diameter of the medicinal fluid inlet, and the second screw-coupling portion is formed as a male-thread-type screw-coupling portion.

Particularly, in order to prevent leakage of drug by a firm coupling force after being coupled to each other, the first screw-coupling portion and the second screw-coupling portion are preferably formed as a square thread form or a trapezoidal thread form. An annular catching step is formed to protrude from an inner side end of the second screw-coupling portion so that, at the time of coupling between the second screw-coupling portion and a non-screw type medical device, the second screw-coupling portion is tightly adhered to and prevented from being separated from an outer circumferential surface at a distal end of a non-screw type medicinal fluid inlet and leakage of drug is prevented.

Hereinafter, features of the present invention will be described in more detail with reference to the accompanying drawings.

Figure 5:
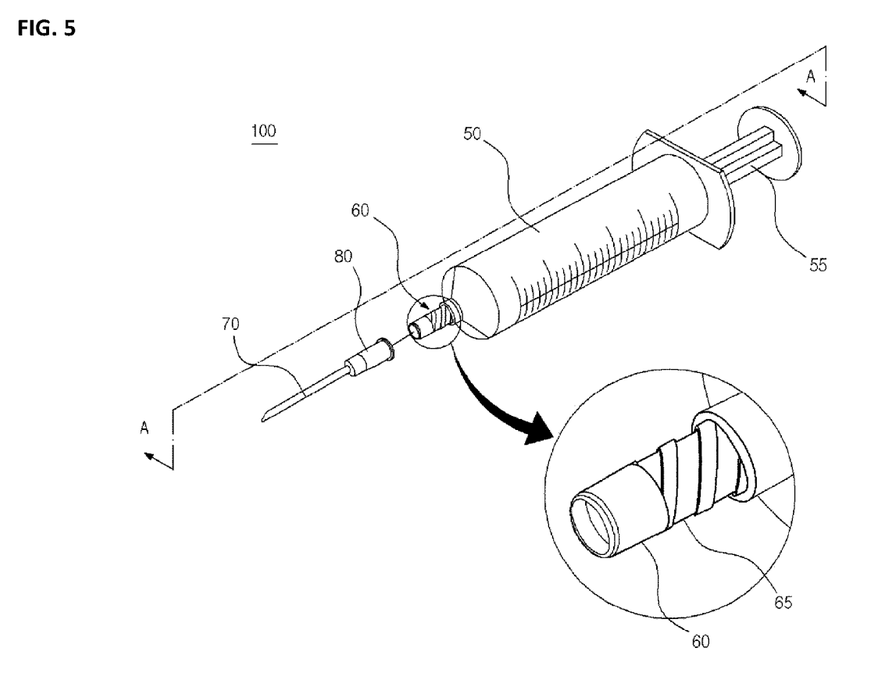
FIG. 5 shows a partially exploded view and an enlarged view of a portion of a syringe set according to the present invention.

FIG. 5 illustrates a perspective view of a state in which a syringe needle hub is separated from a medicinal fluid inlet of a syringe barrel in a syringe set 100 according to the present invention and illustrates an enlarged view of the medicinal fluid inlet.

As illustrated in FIG. 5, the syringe set 100 according to the present invention includes a syringe barrel 50 and a syringe needle hub 80 to which a syringe needle 70 is coupled, wherein a medicinal fluid inlet 60 of a predetermined length is formed at a distal end portion at one side of the syringe barrel 50 so as to serve as a passage that draws drug into the syringe barrel or discharges the drug drawn into the syringe barrel, and a plunger 55 is inserted into an opening of the syringe barrel 50, which is formed at a side opposing the medicinal fluid inlet 60, to allow the drug to be drawn in and injected.

Also, a first screw-coupling portion 65 having a diameter smaller than a reference diameter of the medicinal fluid inlet is formed on an outer circumference at one side of the medicinal fluid inlet 60 of the syringe barrel 50, and a second screw-coupling portion 85 (see FIGS. 6 and 7) having a structure corresponding to the first screw-coupling portion 65 is formed on an inner circumference of the syringe needle hub 80 so as to be fitted and screw-coupled to the first screw-coupling portion 65.

Particularly, in order to allow a firm coupling force to be maintained after being engaged with each other, the first screw-coupling portion 65 and the second screw-coupling portion 85 may be screw-coupled through surface contact with each other while cross-sections of valley portions of the first screw-coupling portion 65 and cross-sections of thread portions of the second screw-coupling portion 85 constitute a square thread form (⊔⊓) or a trapezoidal thread form (⩔⩕).

Figure 6:
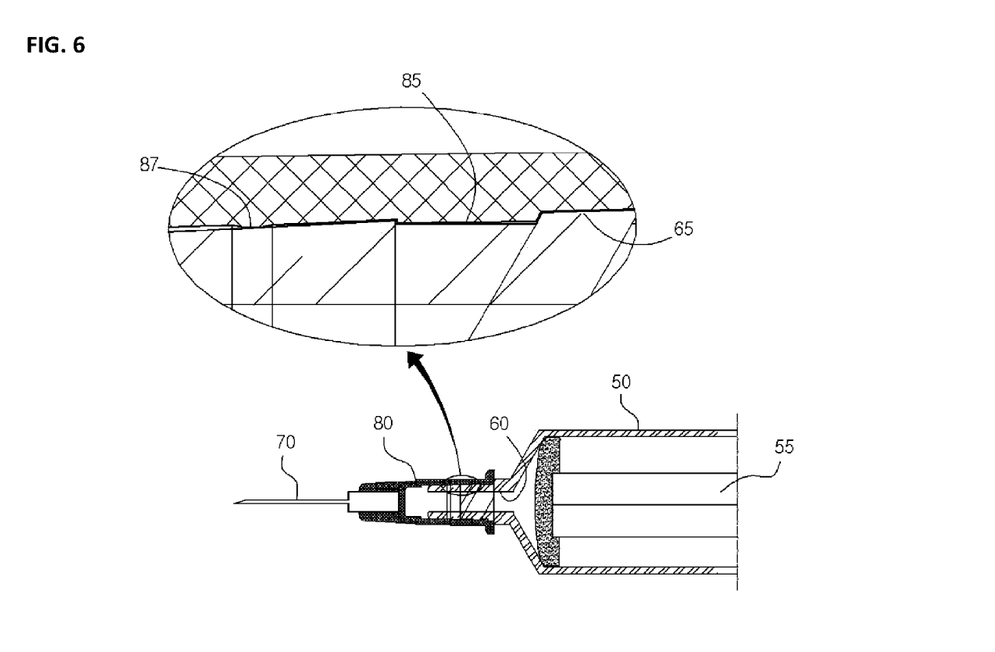
FIG. 6 shows an enlarged cross-sectional view of a portion of a syringe barrel of the syringe set according to the present invention in which a syringe needle hub is coupled to a medicinal fluid inlet.

FIG. 6 illustrates a vertical cross-sectional view taken in a transverse direction of a state in which the syringe needle hub 80 and the medicinal fluid inlet 60 of the syringe barrel 50 are coupled in the syringe set 100 according to the present invention.

As illustrated in FIG. 6, the male-thread-type second screw-coupling portion 85 corresponding to the female-thread-type first screw-coupling portion 65, which is formed on the outer circumference of the medicinal fluid inlet 60 of the syringe barrel 50, is formed on the inner circumference of the syringe needle hub 80, and an annular catching step 87 is further formed to a predetermined height on an inner side end of the second screw-coupling portion 85 in a circumferential direction.

That is, the second screw-coupling portion 85 formed on the inner circumference of the syringe needle hub 80 is screw-coupled to the syringe barrel 50, on which the first screw-coupling portion 65 is formed, or another medicinal fluid connector and provides a firm coupling force, and the annular catching step 87 formed on the inner side end of the syringe needle hub 80 is forcibly fitted and coupled to a distal end of a connecting portion of a non-screw type medical device and, by a firm adhering force, blocks leakage of the drug.

In other words, since an inner diameter of the syringe needle hub 80 on which the second screw-coupling portion 85 is formed is smaller than an inner diameter of a general syringe needle hub not using a screw-coupling method as much as a height to which the second screw-coupling portion 85 protrudes, when the connecting portion of the non-screw type medical device enters the syringe needle hub 80, the distal end portion of the syringe needle hub 80 on which the second screw-coupling portion 85 is formed expands because the distal end portion of the syringe needle hub 80 is made of a plastic material somewhat softer than that of a proximal end portion of the syringe needle hub 80 and has predetermined elasticity.

Therefore, the screw-type syringe needle hub 80 coupled to the outer circumference of the connecting portion of the non-screw type medical device does not come in close contact therewith due to the second screw-coupling portion 85 formed on the inner circumference of the syringe needle hub 80, and thus there is a possibility of drug leakage when drug is supplied. However, in the present invention, the annular catching step 87 is further formed on the inner side end of the syringe needle hub 80 and is forcibly fitted and coupled to an outer circumference of a non-screw type medical device and comes in close contact therewith so that leakage of drug is effectively prevented. In this way, the syringe needle hub 80 may also be used together with a non-screw type medical device.

Figure 7:
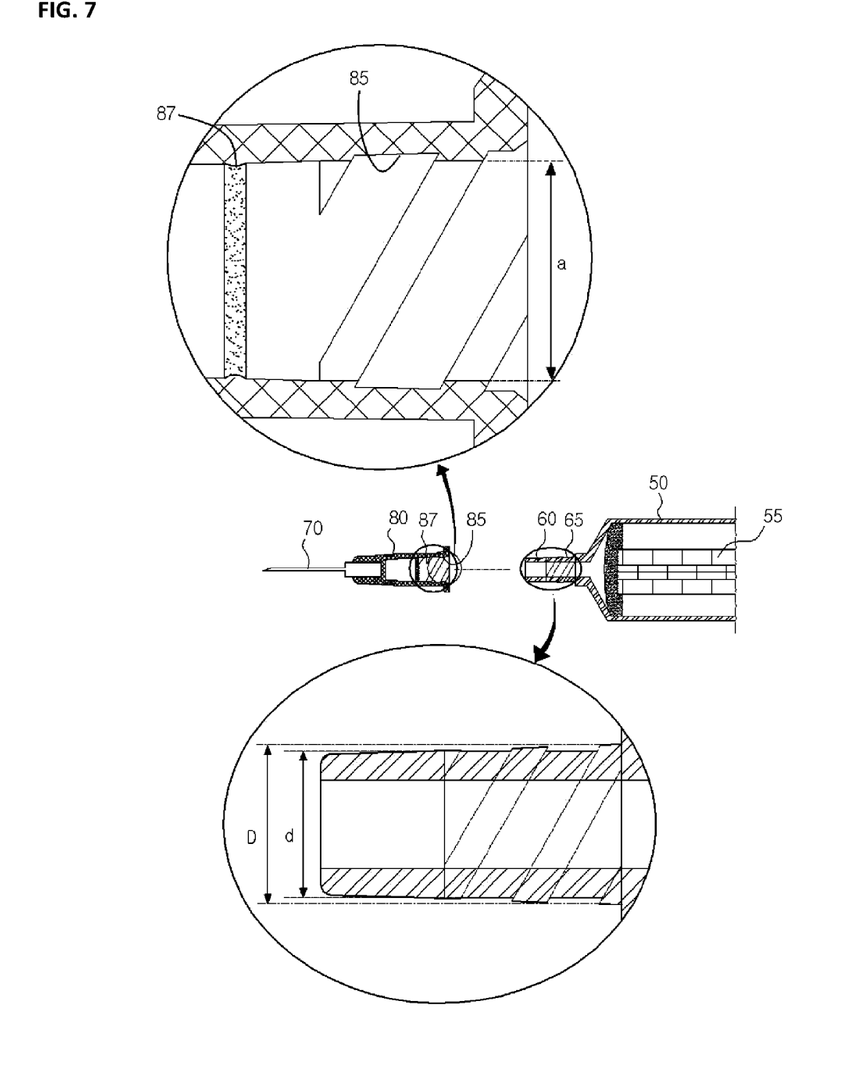
FIG. 7 is a transverse cross-sectional view taken along line A-A of FIG. 5 of a state in which, in the syringe set, the medicinal fluid inlet of the syringe barrel and the syringe needle hub are separated.

The features of the present invention will be described in more detail with reference to FIG. 7 illustrating a cross-section of a state in which the medicinal fluid inlet 60 of the syringe barrel 50 and the syringe needle hub 80 are separated in the syringe set 100 according to the present invention.

The syringe set 100 according to the present invention may provide a firm coupling force as the female-thread-type first screw-coupling portion 65, which is formed on the outer circumference of the medicinal fluid inlet 60 of the syringe barrel 50, and the male-thread-type second screw-coupling portion 85, which is formed on the inner circumference of the syringe needle hub 80, are coupled to each other using a screw-coupling method. Also, since the female and male threads coupled to each other come in surface contact and a contact area increases, the syringe set 100 according to the present invention may effectively prevent leakage of drug.

Particularly, since the first screw-coupling portion 65 formed on the outer circumference of the medicinal fluid inlet 60 according to the present invention has valleys formed to have a diameter d which is smaller than a reference diameter D of the medicinal fluid inlet whose outer diameter is set according to international standards, the first screw-coupling portion 65 may also be forcibly fitted and coupled to a conventional non-screw type syringe needle hub and other medical devices as in the related art. Thus, drug injection is possible, and leakage of drug is prevented when the drug is being injected.

Figure 8:
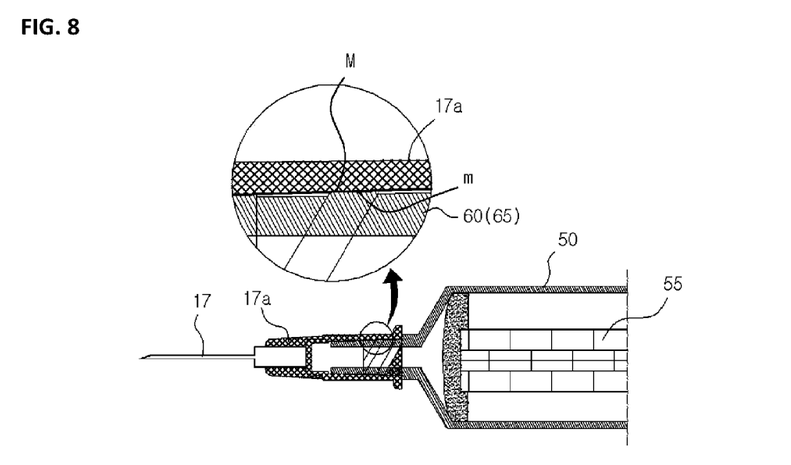
FIG. 8 shows a one-side cross-sectional view and an enlarged view of a portion of the syringe set according to the present invention in a state in which a conventional syringe needle hub is coupled to the medicinal fluid inlet of the syringe barrel that includes a first screw-coupling portion.
Figure 9:
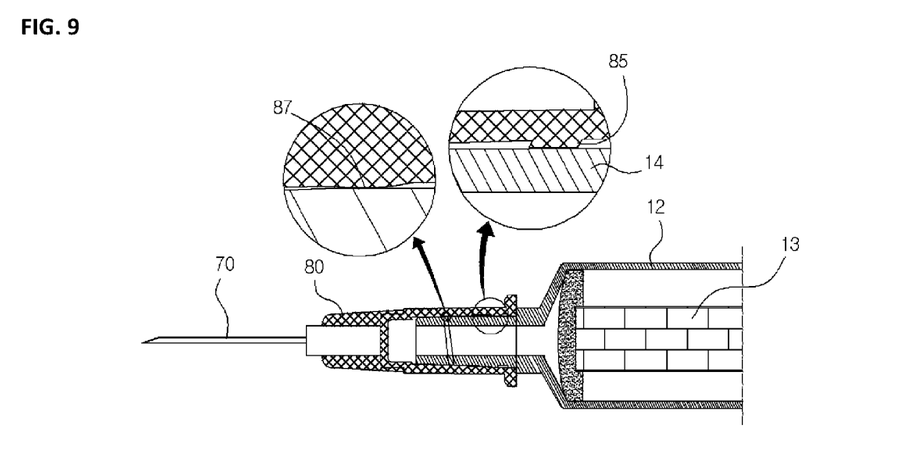
FIG. 9 shows a one-side cross-sectional view and an enlarged view of a portion of the syringe set according to the present invention in a state in which a syringe needle hub of a conventional syringe barrel is coupled to a syringe needle hub including a second screw-coupling portion.

Meanwhile, FIG. 8 shows a cross-sectional view and an enlarged view of a portion of the syringe set according to the present invention in a state in which a conventional syringe needle hub is coupled to the syringe barrel having the medicinal fluid inlet including the first screw-coupling portion. FIG. 9 illustrates a cross-sectional view and an enlarged view of a portion of the syringe set according to the present invention in a state in which the syringe needle hub including the second screw-coupling portion is coupled to a medicinal fluid inlet of a conventional syringe barrel.

As illustrated in FIG. 8, although the first screw-coupling portion 65 is provided on the outer circumference of the medicinal fluid inlet 60 of the syringe barrel 50 according to the present invention, at the time of coupling between the first screw-coupling portion 65 and a conventional syringe needle hub 17a, a surface of a thread m of the first screw-coupling portion 65 that has a horizontal cross-section is forcibly fitted and coupled to an inner circumferential surface M of the conventional syringe needle hub 17a and comes in close contact therewith. Thus, drug supplied to a syringe needle 17 is prevented from leaking to the outside along the inner circumferential surface M of the syringe needle hub 17a.

That is, although the screw-type first screw-coupling portion 65 is formed on the outer circumferential surface of the medicinal fluid inlet 60 provided on the distal end portion at one side of the syringe barrel 50 according to the present invention, the outermost diameter of the first screw-coupling portion 65 is equal to diameters according to international standards, and thus, even when the first screw-coupling portion 65 is coupled to a conventional syringe needle hub not having a screw-coupling structure or another medical device having a conventional forcibly-fitting-coupling structure, the thread m having a flat cross-section may come in close contact with the inner circumferential surface M of a connector at the opposite side, and leakage of drug may be prevented.

Also, since a diameter a of the thread of the second screw-coupling portion 85, which is formed on the inner circumference of the syringe needle hub 80 according to the present invention, is equal to the diameter d of the valley of the first screw-coupling portion 65, the inner diameter of the syringe needle hub 80 is smaller than an inner diameter of the conventional syringe needle hub as much as the height of the thread (see FIG. 7).

Therefore, as illustrated in FIG. 9, at an initial stage in which a non-screw type medicinal fluid inlet 14 of a conventional syringe barrel 12 is being fitted and coupled to the second screw-coupling portion 85 formed on the inner circumference of the syringe needle hub 80 according to the present invention, since the diameter a of the thread of the second screw-coupling portion 85 is smaller than an outer diameter of the medicinal fluid inlet 14 of the conventional syringe barrel 12, a gap may be formed between the inner circumference of the syringe needle hub 80 and the outer circumference of the medicinal fluid inlet 14 of the conventional syringe barrel 12 as an inlet side of the syringe needle hub 80 is forcibly widened.

However, when the conventional syringe barrel 12 is pushed further into the syringe needle hub 80, as the outer circumference of the medicinal fluid inlet 14 of the conventional syringe barrel 12 is forcibly fitted and coupled to the annular catching step 87 provided on the inner side end of the syringe needle hub 80, the inner circumference of the syringe needle hub 80 and the outer circumference of the medicinal fluid inlet 14 may maintain a state of being in close contact.

Therefore, even when the second screw-coupling portion 85 side provided on the distal end portion of the syringe needle hub 80 and the outer circumference of the medicinal fluid inlet 14 do not come in close contact, the catching step 87 allows the close contact therebetween, and the risk of drug leakage when drug is injected through a syringe needle is eliminated. Thus, the syringe needle hub 80 according to the present invention may be used in combination with the conventional syringe barrel or other medical devices.

In this way, the syringe set according to the present invention allows a firm coupling state to be maintained not only at the time of coupling between parts using a screw-coupling method but also at the time of coupling between a part using the screw-coupling method and a part not using the screw-coupling method. The syringe set according to the present invention includes the first and second screw-coupling portions having a particular structure that prevents leakage of drug so that, during use of the syringe set and other medical devices at the medical site, the syringe set and other medical devices may be engaged and compatibly used with other medical devices and syringes and may be prevented from being arbitrarily separated while drug is being injected. Therefore, it is possible to provide advantageous effects in that the patient's pain is reduced and the drug leakage problem is addressed.

The disposable syringe set with improved engageability according to the present invention that has the above described configuration and structure not only allows coupling between medical devices having screw-coupling portions having the same structure but also allows coupling between a medical device having a screw-coupling portion and a medical device not having a screw-coupling structure and, particularly, prevents leakage of drug at the time of coupling between different types of medical devices having a screw coupling portion and not having a screw-coupling structure. In this way, it is possible to provide an easy-to-use syringe set that can be engaged with any medical device so that the versatility of the syringe set is further extended.

An embodiment in which the first and second screw-coupling portions are formed in a syringe set has been described above in the detailed description of the present invention. However, the first screw-coupling portion or second screw-coupling portion disclosed in the embodiment of the present invention may also be formed in a medical device other than the syringe set, such as a medicinal fluid connector, to reduce the patient's pain and further improve convenience of healthcare workers in giving medical care.

DESCRIPTION OF REFERENCE NUMERALS

| | |
|---|---|
| 12: syringe barrel | 14: medicinal fluid inlet |
| 17: syringe needle | 17a: syringe needle hub |
| 50: syringe barrel | 55: plunger |
| 60: medicinal fluid inlet | 65: first screw-coupling portion |
| 70: syringe needle | 80: syringe needle hub |
| 85: second screw-coupling portion | 87: catching step |
| 100: syringe set | |

What is claimed is:

1. A syringe set with improved engageability, the syringe set having a structure comprising:
   a syringe barrel in which a medicinal fluid inlet of a predetermined length is formed to protrude at one side and a plunger is fitted and coupled to an opening at the other side;
   a first screw-coupling portion formed on an outer circumference of the medicinal fluid inlet;

a syringe needle hub in which a syringe needle is provided and which is configured to be fitted and coupled to the outer circumference of the medicinal fluid inlet; and a second screw-coupling portion formed on an inner circumference of the syringe needle hub and configured to be coupled to the first screw-coupling portion, wherein the first screw-coupling portion is formed as a female-thread-type coupling portion having a diameter (d) smaller than a reference diameter (D) of the medicinal fluid inlet, configured to be compatible with a non-thread-type syringe needle hub, the second screw-coupling portion provided on the inner circumference of the syringe needle hub is formed as a male-thread-type coupling portion configured to be coupled to the female-thread-type coupling portion and to be compatible with a non-thread-type medicinal fluid inlet, and a catching step having an annular shape is formed to protrude a predetermined height from an inner side of the male-thread-type coupling portion formed on the inner circumference of the syringe needle hub, the female-thread-type coupling portion and the male-thread type coupling portion are coupled to each other in surface contact to prevent leakage of a medicinal fluid through the surface contact, the catching step is formed by a protrusion protruding radially inwardly from the inner circumference of the syringe needle hub, and the catching step is forcibly fitted into the outer circumference of a distal end portion of the medicinal fluid inlet to prevent leakage of a medicinal fluid, the catching step is located farther from the syringe barrel than an area which the female-thread-type coupling portion and the male-thread-type coupling portion are coupled to each other in surface contact, wherein the second screw-coupling portion is formed on a distal end portion of the syringe needle hub and wherein the distal end portion of the syringe needle hub is made of a plastic material softer than that of a proximal end portion of the syringe needle hub.

* * * * *